United States Patent
Buzzi

(10) Patent No.: US 11,235,078 B2
(45) Date of Patent: Feb. 1, 2022

(54) DEVICE FOR SANITIZING AIR-CONDITIONERS

(71) Applicant: Marco Buzzi, Milan (IT)

(72) Inventor: Marco Buzzi, Milan (IT)

( * ) Notice: Subject to any disclaimer, the term of this patent is extended or adjusted under 35 U.S.C. 154(b) by 0 days.

(21) Appl. No.: 15/326,556

(22) PCT Filed: Jul. 23, 2015

(86) PCT No.: PCT/IB2015/055574
§ 371 (c)(1),
(2) Date: Jan. 16, 2017

(87) PCT Pub. No.: WO2016/012966
PCT Pub. Date: Jan. 28, 2016

(65) Prior Publication Data
US 2017/0197000 A1    Jul. 13, 2017

(30) Foreign Application Priority Data

Jul. 24, 2014    (IT) .......................... MI2014A001355

(51) Int. Cl.
*A61L 2/07*    (2006.01)
*A61L 2/26*    (2006.01)
(Continued)

(52) U.S. Cl.
CPC .................. *A61L 2/07* (2013.01); *A61L 2/26* (2013.01); *B08B 3/026* (2013.01); *B08B 3/08* (2013.01); *F24F 1/00* (2013.01); *F28G 1/02* (2013.01); *F28G 1/166* (2013.01); *F28G 9/00* (2013.01); *B08B 2203/0229* (2013.01); *F24F 2221/225* (2013.01); *F28F 2265/20* (2013.01)

(58) Field of Classification Search
CPC .............. A61L 2/07; A61L 2/26; B08B 3/026
See application file for complete search history.

(56) References Cited

U.S. PATENT DOCUMENTS

| 6,589,478 B1 * | 7/2003 | Keim .................. A61L 2/07 422/26 |
| 2003/0024552 A1 | 2/2003 | Watanabe |
| 2014/0359965 A1 * | 12/2014 | Hansen ............... A47L 11/4083 15/320 |

FOREIGN PATENT DOCUMENTS

| CN | 201267817 Y | 7/2009 |
| CN | 201327164 Y | 10/2009 |

(Continued)

OTHER PUBLICATIONS

International Search Report And Written Opinion For International Application No. PCT/IB2015/055574 (dated Nov. 17, 2015) (9 Pages).

(Continued)

*Primary Examiner* — Kevin Joyner
(74) *Attorney, Agent, or Firm* — Steinfl + Bruno LLP

(57) ABSTRACT

A device for sanitizing a unit of an air conditioning system having a source of sanitizing fluid, means for the controlled delivery of a jet of sanitizing fluid, suctioning means to generate suction flow is provided. The device has suction opening shaped to direct the suction flow towards a determined direction with respect to the direction of the jet of sanitizing fluid. The suction opening is smaller than the unit of the air conditioning to be sanitized in order to be alternately moved from a first portion of the unit towards a second portion of the same unit.

14 Claims, 3 Drawing Sheets

(51) Int. Cl.
    *B08B 3/02*         (2006.01)
    *F28G 9/00*        (2006.01)
    *B08B 3/08*         (2006.01)
    *F24F 1/00*         (2019.01)
    *F28G 1/02*        (2006.01)
    *F28G 1/16*        (2006.01)

(56) References Cited

FOREIGN PATENT DOCUMENTS

| | | | |
|---|---|---|---|
| FR | 2963826 | A1 | 2/2012 |
| JP | 2005214600 | A | 8/2005 |
| WO | 03057378 | A1 | 7/2003 |

OTHER PUBLICATIONS

Italian Search Report for Italian Application No. MI20141355 (dated Apr. 20, 2015) (2 Pages).

\* cited by examiner

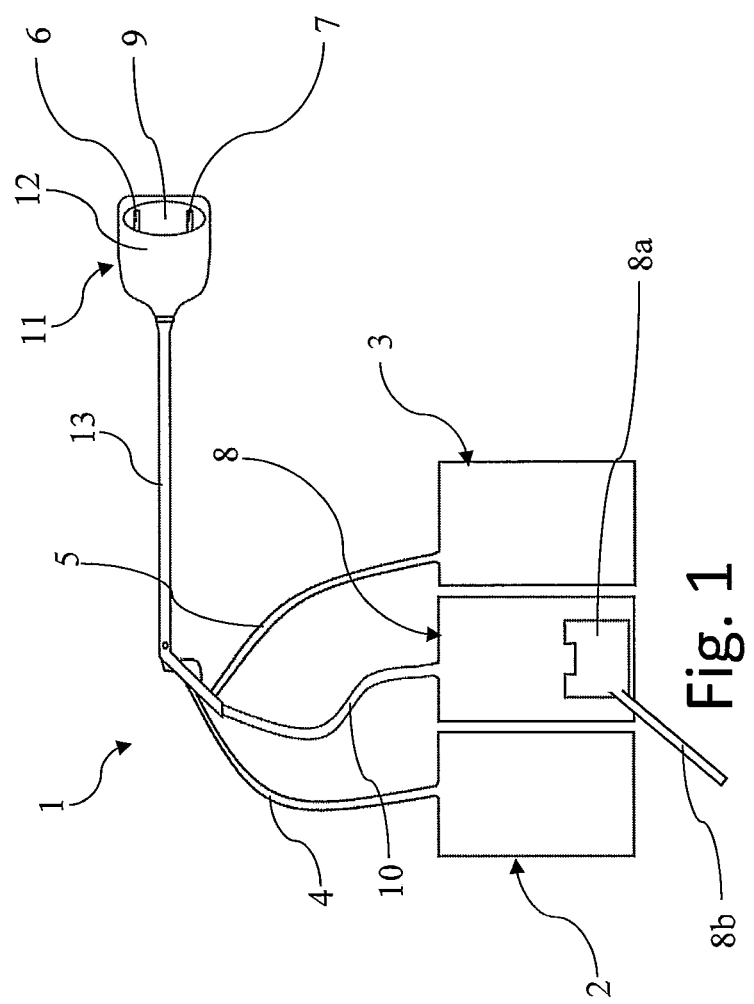

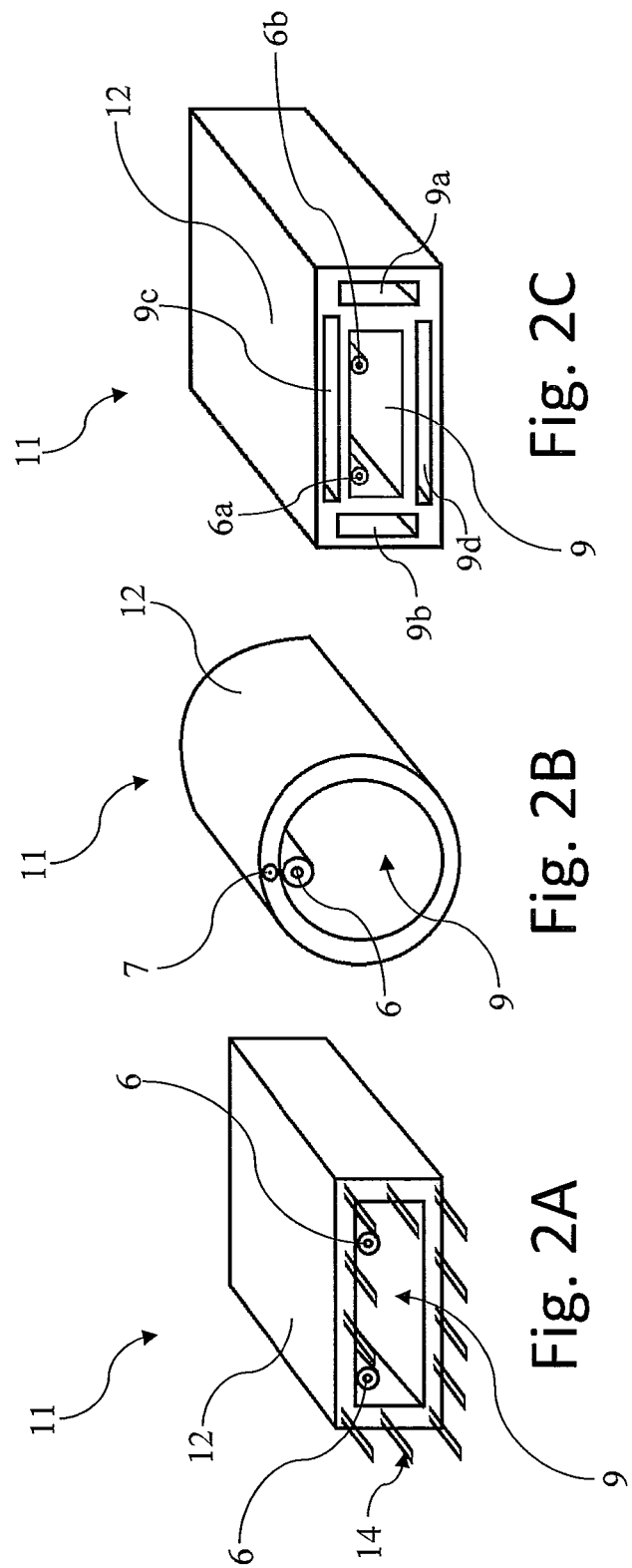

DEVICE FOR SANITIZING AIR-CONDITIONERS

CROSS-REFERENCE TO RELATED APPLICATIONS

This application is a 371 of PCT/IB2015/055574 filed Jul. 23, 2015, which claims the benefit of Italian Patent Application No. MI2014A001355 filed Jul. 24, 2014.

FIELD OF THE INVENTION

The present invention concerns a device for sanitizing at least one indoor and/or outdoor unit of an air conditioning system. Preferably, the device is adapted to the microbiological sanitization of indoor and outdoor terminal units of the conditioning system.

KNOWN BACKGROUND ART

Conditioning systems allow the parameters of relative humidity, temperature and air speed in a particular environment to be changed in order to ensure thermohygrometric conditions that are adequate for the use of that environment by man, at any outside weather condition.

The operation of an air conditioner is based on carrying out a thermodynamic cycle on a heat-transfer fluid which is circulated between two separate units: an outdoor unit housing the conditioner motor; an indoor unit (usually called split) providing the circulation of air (conditioned or not) by spreading it across the rooms through a dedicated slit.

The task of the outdoor unit is to compress the heat-transfer fluid leading it to high pressures and temperatures by means of a compressor; then, by means of fans and heat exchangers, the fluid transfers heat to the external environment thereby lowering its own temperature. Before the fluid is injected again into the indoor unit, its pressure is lowered by means of an evaporator. The pressure reduction causes the heat-transfer fluid reaching the indoor terminal unit of the system to cool down. The indoor units, by means of fans, draw the warm air from the indoor environment and convey it towards the heat exchangers. Air transfers its heat to the heat-transfer fluid before being released back into the indoor environment once cooled. Then, the heat-transfer fluid carries the heat absorbed from the indoor environment and releases it into the outdoor environment by means of the heat exchangers of the outdoor unit. Not only the indoor units carry out the functions of controlling the thermal conditions but also of filtering all particles dispersed in the air. The air drawn, cooled and released back into the indoor environment is filtered and possibly dehumidified inside the split unit. As a result of these functions, chemical and microbiological contaminants accumulate and can saturate the system therefore transforming it, paradoxically, into a source of pollution and contamination. In addition to the obvious sanitary implications, a dirty conditioner causes a lower efficiency of the system and, therefore, the energy efficiency decreases and the energy waste raises. For example, the dust accumulation on fans may cause a decrease in the air flow through the heat exchanger thereby resulting in a decrease in the cooling or heating effect of the air-conditioner.

For these reasons it is useful to periodically sanitize the conditioning system and, in particular, the terminal units of the system. Often conditioning systems comprise a plurality of indoor terminal units connected to one or more outdoor units. Although the maintenance of the outdoor units is not a particularly onerous operation, the sanitization of the indoor units can be time-consuming and expensive especially in large public or private structures such as offices, hotels, hospitals etc., where there is a large number of indoor units to be periodically sanitized.

In order to carry out the sanitizing of the split units, it is possible for example to remove the shell thereof, then suction the solid particles accumulated inside it and subsequently carry out the actual sanitizing step in which the inside of the unit is manually cleaned by means of microfiber cloths and germicidal products able to drastically reduce the bacterial load as well as to prevent its formation for a certain period of time. The required labor cost for this operation is very high especially when a large number of indoor and/or outdoor units have to be sanitized in a reasonable time. Furthermore, by manually disassembling and cleaning the individual units, the health of the workers is put in danger, because they have to be in contact for a long time with pollutants such as mold, fungi, yeasts, mites, viruses and bacteria such as Legionella, a dangerous Gram-negative bacterium which, in some cases, can result in death.

In order to speed up the sanitization of split units, devices are known which, by means of a high pressure steam jet, allow sterilizing the inside of the air conditioner so as to avoid the manual cleaning by means of microfiber cloths and germicidal products. However, during the delivery of the steam jet, condensation forms that, during the sanitizing step, can dirty walls, floor, or furniture near the split unit. Therefore, to overcome this problem, the environment must be prepared for sanitation by placing drop cloths in the areas near the split unit. Although this solution speeds up the sanitization of the air-conditioner with respect to the technique in which the operator has to manually clean the internal parts of the split, however it is not able to reduce the risk for the health of the worker who, while carrying out sanitization, could come in contact with the condensation produced by the steam. For the sanitization of air conditioners other devices are known, the latter being provided with a protective housing, namely a casing, suitable to be fixed to the split unit or to the wall surrounding it, so as to isolate the split unit from the operator. In practice, the housing surrounds the split unit and forms a sanitizing chamber in which the steam is injected. The condensation produced by the steam is then collected inside the housing and conveyed to a storage tank by a discharge duct. FR-A-2963826 describes a similar sanitizing device for indoor split units, having suctioning means associated therewith, the latter being fluidically connected to the casing intended to completely confine the indoor unit to be sanitized.

Even this solution is not free from drawbacks, in fact the split units are often positioned in areas difficult to be accessed and where it is not easy to safely and quickly fix a containment housing for collecting the steam condensation.

In addition, since the housing surrounds the entire split unit, it is not possible for the operator to see and check if any parts are still to be sanitized, so that it is often necessary to deliver a greater steam amount with respect to that required to obtain a complete sanitization. In this way, the energy and the execution time required to sanitize every single split units are greater with respect to the solution in which the steam jet is used without the protective casing. In fact, once the steam delivery step is concluded, it is however necessary to wait until all the condensation produced by the steam falls by gravity into the housing before removing the latter. In order to prevent condensation drops from falling, the protective casing can be removed when the split unit is substantially dry. Therefore, these operations have to be carried out by skilled labor.

Although the solutions proposed by the prior art are able to speed up the sanitation of the split unit, however they are not totally safe for the operator. Similarly, the solutions ensuring adequate safety for the operator result in an increase both of time and energy required to sanitize the split units, thus turning out to be inefficient.

SUMMARY OF THE INVENTION

Object of the present invention is to overcome the problems briefly discussed above of the known prior art, and to provide a device for sanitizing an air conditioning system which allows indoor and outdoor terminal units of the conditioning system to be sanitized in a quick and safe way for the operator.

It is a further object of the present invention to provide a device for sanitizing an air conditioning system also usable by not skilled labor.

It is a further object of the present invention to provide a method for sanitizing an air conditioning system that allows the whole sanitizing process to be carried out more efficiently in terms of time and energy with respect to the known prior art.

The present invention achieves these and other objects through a device for sanitizing at least one indoor and/or outdoor unit of a conditioning system according to claim 1 and the respective dependent claims, and a method for sanitizing a conditioning system according to claim 14 and the respective dependent claims.

Hereinafter reference will be made to indoor units of a conditioning system, but the present invention can also be used for sanitizing outdoor units. In particular, indoor units mean all kinds of units adapted to supply conditioned air inside the rooms. Although for greater simplicity of discussion reference will be made to split units, the present invention can also be used for sanitizing all kinds of indoor or outdoor units, such as fan coil units, evaporators, condensing units and floor, ceiling and cassette units, etc.

In particular, according to the present invention the device for sanitizing at least one indoor and/or outdoor unit of a conditioning system comprises a source of sanitizing fluid, means for the controlled delivery of one or more jets of sanitizing fluid and suctioning means to generate at least one suction flow. The device comprises at least one suction opening shaped so as to direct the suction flow towards a determined direction with respect to the direction of the jet of sanitizing fluid. Furthermore, said suction opening is sized so as to be smaller than the unit to be sanitized in order to move said opening from a first portion of said unit towards at least one second portion of the same unit.

In other words, the suction opening of the device according to the invention is shaped so as to engage only one area (or portion) of the unit to be sanitized, i.e. without engaging and surrounding the entire outdoor and/or indoor unit that is being sanitized.

By way of example, the section of the suction opening intended to engage the unit to be sanitized can be rectangular and preferably sized so that its width ranges from 4 cm to 15 cm and its height from 1.5 cm to 15 cm. As a further example, the suction opening can be rectangular and have a width of 10 cm and a height of 2 cm, or even width of 10 cm and height still of 10 cm.

This feature allows a conditioning system to be sanitized without placing protective housings for collecting condensation produced by the sanitizing fluid, further allowing the operator to position the suction opening in a safe, extremely precise, i.e. effective, way at the different portions of the unit of the conditioning system.

In this way the operator, besides delivering the sanitizing fluid, can also precisely direct a suctioning fluid having a direction such as to remove all condensation and contaminants which are inside the unit of the conditioning system under sanitization in a simple, quick and safe way.

The source of sanitizing fluid comprises, according to a preferred aspect of the present invention, a pump or a nebulizer to produce a jet of a biocidal fluid (preferably liquid or possibly nebulized) and/or a steam generator, therefore sanitizing fluid means herein a jet of biocidal fluid and/or saturated steam at about 160° C.

Preferably, the device according to the invention comprises a delivering head, also sized so as to be smaller than the unit to be sanitized, to be alternately moved from a first portion of said unit towards at least one second portion of the same unit, in which the nozzles for the delivery of sanitizing fluid as well as the suction opening are housed.

Namely, preferably, the afore said delivering head is sized so as to engage only an area (or portion) of the indoor and/or outdoor unit to be sanitized, thus without being able to surround such unit, thereby turning out to be usable in a safe, handy and precise way.

For example, the delivering head may be rectangular with a width of up to 20 cm and height up to 20 cm.

For example, the operator can easily and quickly position the delivering head next to a portion of the split unit by means of a stem, having a full view of the split unit during the sanitization. The operator is therefore able to precisely direct one or more jets of sanitizing fluid towards a portion to be sanitized with a determined direction. The suction opening is shaped so as to allow to safely and efficiently suction every drop of condensation and/or biocidal fluid produced by the sanitization, thus guaranteeing adequate safety to the operator without having to position drop cloths on the walls and/or on the floor.

Thanks to the present invention the operator can deliver one or more jets of sanitizing fluid (steam and/or biocidal fluid) towards a portion of the outdoor and/or indoor unit, splits and/or condensing units, while simultaneously suctioning the condensation and/or excess biocidal fluid thereby sanitizing such portion and leaving it dry.

The suction opening is shaped so as to direct a suction flow having a determined direction with respect to the direction of the jet of sanitizing fluid. The delivering head can accommodate one or more suction openings to direct one or more suction flows having specific directions depending on the situation in which the operator has to carry out the sanitization. In fact, the delivering head can be advantageously disconnected from the device and replaced by another delivering head housing a different number of nozzles for the sanitizing fluid and/or a different number of suction openings shaped so as to fulfill various functions described in more detail in the following of the present description.

In any case, the delivering head is shaped such that at least one nozzle for delivering sanitizing fluid is positioned inside the delivering opening and/or that the direction of at least one suction flow is parallel to the direction of at least one jet of sanitizing fluid.

The device of the present invention allows to individually or simultaneously control the suction flow rate generated by the suctioning means, the pressure of the steam produced by the steam generator and the flow rate of the delivered biocidal fluid, thereby allowing optimizing time and energy required to complete a proper sanitization of the conditioning system. Both the method and the device according to the present invention can be also used by not-skilled labor thereby further cutting costs for sanitizing the split units of a conditioning system.

BRIEF DESCRIPTION OF THE DRAWINGS

Further aspects and advantages of the present invention will become more evident from the following description, made for illustration purposes and without limitation, with reference to the accompanying schematic drawings, in which:

FIG. 1 is a block diagram of an embodiment of the device according to the present invention;

FIGS. 2A-2C are perspective views of some particular embodiments of the delivering head of the device according to the present invention;

DETAILED DESCRIPTION OF SOME EMBODIMENTS OF THE INVENTION

Figure 3A:
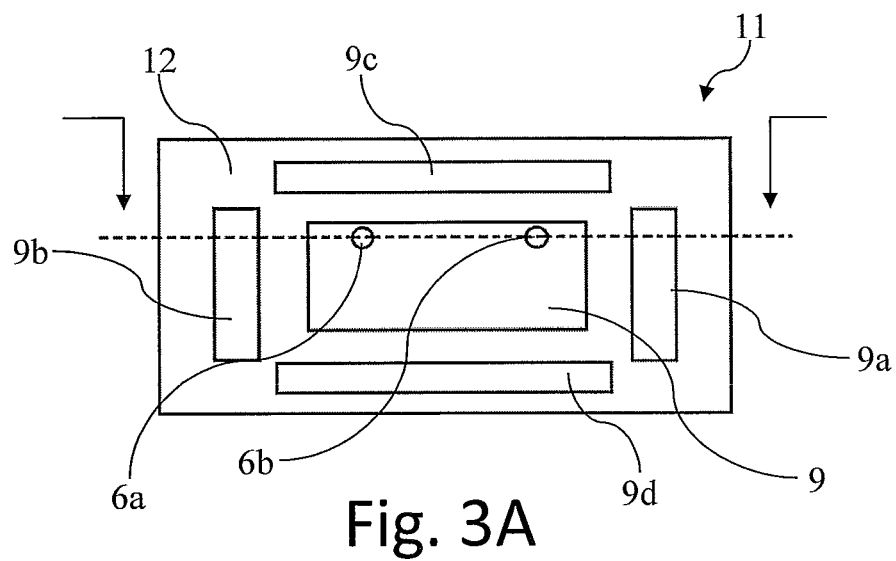
FIGS. 3A and 3B are front and sectional views, respectively, of a particular embodiment of the delivering head of the device according to the present invention.

FIG. 1 shows a device 1 for sanitizing at least one indoor and/or outdoor unit of an air conditioning system comprising a source 2, 3 of sanitizing fluid. The sanitizing fluid can be a biocidal fluid (preferably liquid and/or biodegradable) and/or saturated steam. In the shown embodiment, the source of sanitizing fluid comprises a steam generator 2, able to produce saturated steam at about 160° C. at a pressure of about 9 bar, and a pump 3 for producing a jet of biocidal fluid, possibly nebulized.

The device 1 comprises means for the controlled delivery of at least one jet of sanitizing fluid. Preferably, both the steam generator 2 and the pump 3 are hydraulically connected to means for the controlled delivery of the sanitizing fluid which, in the embodiment shown in FIG. 1, comprise a first nozzle 6 for delivering a steam jet and a second nozzle 7 for delivering a jet of biocidal fluid. In FIG. 1, the connection between the source of sanitizing fluid and means for the controlled delivery is symbolically denoted by the ducts 4, 5 respectively connecting the steam generator 2 to the nozzle 6 and the pump 3 to the nozzle 7. By means known in the art (for example, mechanically or electrically operated valves) it is therefore possible to enable or disable the delivery of steam and/or biocidal fluid through the respective nozzles 6 and/or 7. Preferably, it is possible to adjust the steam pressure between 5 and 10 bar and/or adjust the flow of biocidal liquid by changing the pump speed. Preferably, the pump flow rate can be of about 46 l/s, mostly of about 22 kPa.

In a preferred embodiment, the connection between the source of sanitizing fluid and the means for the controlled delivery is provided through a single duct which hydraulically connects a pump to one or more nozzles for delivering the sanitizing fluid. By means of additional ducts, the pump draws steam and biocidal liquid respectively from the steam generator and from one or more tanks of germicidal products. Such a solution allows different germicidal products to be mixed with steam and the sanitizing fluid to be delivered in the form of one or more jets of boiling liquid.

In a further embodiment it is possible to provide a heating circuit in order to raise the temperature of the biocidal liquid without having to mix the biocidal liquid with steam and possibly without providing a steam generator.

Referring to FIG. 1, the device 1 further comprises suctioning means 8 fluidically connected to at least one suction opening 9.

In FIG. 1, a duct 10 symbolically indicates the connection between the suctioning means 8 and the suction opening 9. The suctioning means 8 are known per se in the art and preferably comprise an aspirator able to suction liquid and/or solid materials drawing them through the suction opening and conveying them into a storage tank 8a. The storage tank can be provided with a discharge duct 8b to empty the tank 8a of the materials suctioned during sanitization without having to disconnect the tank 8a from the device 1 and, possibly, without having to suspend the sanitization of the conditioning system.

The suction opening 9 is shaped so as to direct a suction flow towards a determined direction with respect to the direction of the jet of sanitizing fluid delivered by the nozzles 6, 7. Furthermore, advantageously, the suction opening 9 is sized so as to be smaller than the unit of the conditioning system to be sanitized, so that this suction opening 9 can be moved from a first portion (or area) of said unit towards at least one second portion (or area) of the same unit, separated from the afore said first portion. As clear to the person skilled in the art, the small size of the suction opening 9 not only allows to limit the bulk of the sanitizing device 1 making it extremely easy to be handled, but also allows the operator to position, in an extremely precise way and in total safety, this suction opening 9 of the device 1 on various portions of the unit of the conditioning system depending on the need detected by the operator to more or less strongly exert the suctioning action of the sanitizing fluid.

Preferably, the device 1 comprises a delivering head 11 constituted by a body 12 in which the nozzles 6, 7 and the suction opening 9 are housed.

Also the delivering head 11, preferably substantially delimiting the above said suction opening, is sized so as to be smaller than the unit of the conditioning system to be sanitized, so that it can be moved, for example in an alternate way, from a first portion (or area) of said unit towards at least one second portion (or area) of the same unit of the conditioning system, separate from the first portion (area) of the latter.

In other words, the delivering opening 9 and preferably the respective delivering head 11 are sized so that they can not be overlapped on the entire indoor and/or outdoor unit of a conditioning system to be sanitized, so they engage only separate areas of the same indoor and/or outdoor unit, thereby allowing the operator to direct, in a completely safe, easy and precise way, the suction flow, and preferably also the flow of sanitizing fluid, where it is most needed on the unit being sanitized, only with the help of the view.

The operator can move the delivering head and direct the jet of sanitizing fluid towards a specific portion of the indoor and/or outdoor unit, the split and/or condensing unit to be sanitized, by means of a stem 13 the delivering head 11 can be removably constrained to. During the delivery of the sanitizing fluid (steam and/or biocidal liquid), the suction flow coming from the suction opening 9 is directed in parallel to the jet of sanitizing fluid. As the sanitizing fluid hits the portion of the split unit, due to the condensation of the delivered steam and/or biocidal liquid, it generates drops which are removed by the suction flow, thus keeping dry and sanitized the portion of the split unit.

Even not-skilled labor can carry out a precise sanitization of the split units in complete safety, without using drop clothes and/or housings for collecting condensation. In fact, during the delivery of saturated steam, also dust particles, mold, bacterial colonies, viruses and other contaminants trapped inside the split and/or condensing unit will be suctioned without the danger of being shot out of the suction flow.

As previously explained, the delivering head 11 can be disconnected from the device 1 and replaced by other delivering heads generally comprising at least one nozzle for delivering a jet of sanitizing fluid and one or more suction openings, each shaped so as to direct a suction flow towards a determined direction with respect to the jet of sanitizing fluid.

In particular, FIGS. 2A-2C show some possible shapes of the delivering head 11 of the device 1.

FIG. 2A shows a delivering head 11 constituted by a body 12 in which two nozzles 6 for delivering steam and a suction opening 9 are housed. In particular, both the nozzles 6 are positioned inside the suction opening. In this embodiment, the suction opening 9 is shaped so that the direction of the suction flow is parallel to both the steam jets delivered by the nozzles 6.

The delivering head 11 further comprises means 14 to confine a portion of a unit of a conditioning system and/or to remove mechanically liquid and/or solid particles from the portion of a unit of a conditioning system. The means 14 allow the contaminants to be removed from the portion of the conditioning system by coupling with mechanical wiping and/or bearing, thereby reducing the time and energy to carry out the sanitization.

In a preferred embodiment of the present invention, the delivering head 11 shown in FIG. 2A comprises a comb having bristles arranged around the suction opening 9 and around the nozzles 6.

Further embodiments may provide the means 14 comprising one or more combs (or brushes) equipped with bristles and/or hairs and/or lints, in general rigid or flexible bodies made, for example, of fabric and/or nonwoven fabric and/or rubber, to mechanically remove solid and/or liquid particles from the portion of the unit of conditioning system to be sanitized.

Thanks to the particular geometrical arrangement of the means 14 shown in FIG. 2A, two actions can be simultaneously carried out: mechanically remove liquid and/or solid particles from a portion of the unit of the conditioning system (for example a portion of split and/or condensing unit) and confine the portion of the unit of conditioning system during the sanitization. The confinement is carried out by leaning the means 14 against the unit portion to be sanitized. In this way the suction flow is improved, being concentrated on a unit portion confined by the means 14, thereby further reducing the probability that sanitizing fluid, condensate or contaminants can escape the suction flow.

Further embodiments may provide a delivering head 11 comprising means 14 only adapted to confine a portion of a split unit, for example by means of at least one body or at least one substantially cylindrical wall, for example funnel-shaped (made of rigid or flexible material) and arranged so as to surround at least one suction opening and/or the nozzles for delivering the sanitizing fluid.

Otherwise, further embodiments may provide a delivering head 11 comprising means 14 only adapted to mechanically remove solid or liquid particles from a portion of a unit of the conditioning system. In the latter case the means 14 are made similarly to those shown in FIG. 2A, i.e. with one or more combs (or brushes) provided with bristles and/or hairs and/or lints, in general rigid or flexible bodies made for example of fabric, nonwoven fabric, rubber, but with a different geometrical arrangement, for example with the bristles arranged on the delivering head in one or more rows parallel to each other.

FIG. 2B shows a delivering head 11 constituted by a body 12 having a substantially cylindrical shape. The delivering head comprises a suction opening 9, a nozzle 6 for delivering steam and a nozzle 7 for delivering a jet of biocidal liquid. Also in this embodiment, the suction opening 9 is shaped so that the direction of the suction flow is parallel to both the jets of sanitizing fluid delivered by the nozzles 6 and 7.

FIG. 2C shows a further embodiment of the delivering head 11 in which four auxiliary suction openings 9a, 9b, 9c, 9d, positioned around a central suction opening 9, are provided. The delivering head 11 comprises two nozzles 6a, 6b for delivering steam and positioned inside the central suction opening 9.

Figure 3B:
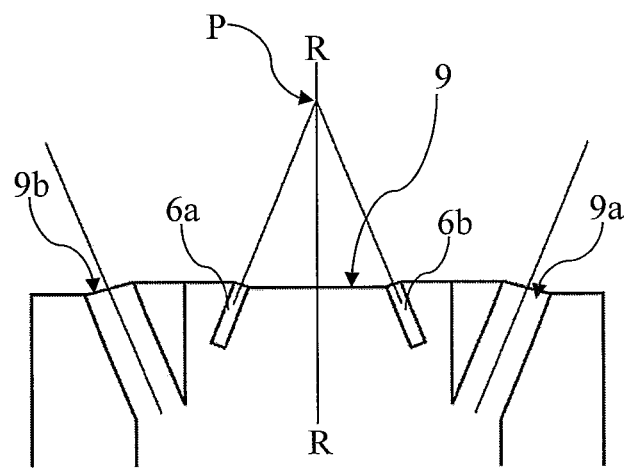

As shown in FIGS. 3A and 3B, the nozzles 6a, 6b are positioned so as to deliver two steam jets tilted with respect to the longitudinal axis R-R of the delivering head 11 and incident at an intersection point P. The central suction opening 9 is shaped so as to direct a suction flow parallel to the longitudinal axis of the dispensing head, whereas the auxiliary openings 9a and 9b are shaped so as to direct a suction flow parallel to the respective steam jets delivered by the nozzles 6a and 6b.

Similarly, also the suction openings 9c, 9d can be shaped so as to direct the suction flows to be symmetrically tilted with respect to the longitudinal axis R-R. This solution is very advantageous when the steam delivery takes place at high pressures, in fact, the suction flows from the auxiliary suction openings allow creating a substantially funnel-shaped suction wall and able to suction the condensed sanitizing fluid even when the latter is delivered at high pressures, for example higher than 9 bars.

Thanks to the device 1 it is therefore possible to carry out a method for sanitizing a conditioning system comprising the following steps. The operator places the delivering head 11 and the respective suction opening 9 next to a first portion of the split unit to be sanitized. Then, the suctioning means 8 can be activated by the operator in order to generate at least one suction flow. Right at the suction time, or immediately after, the operator activates the means for the controlled delivery of at least one jet of sanitizing fluid and directs the sanitizing fluid towards the portion to be sanitized. During this last step, the operator can activate the steam generator and/or the pump to deliver the biocidal liquid. When the portion of the split and/or the condensing unit is properly sanitized, the operator moves the dispensing head to a second portion to be sanitized and separate from the first, already sanitized, portion. During the movement, the delivery of sanitizing fluid and the suction of the condensation can be advantageously continued, so that no portion of the split unit is left not completely sanitized.

The invention claimed is:

1. A sanitation device for a unit of an air conditioning system, the sanitation device comprising:
   a delivering head;
   an aspirator configured to generate a suction flow;
   a suction opening connected to the aspirator, the suction opening being configured to direct the suction flow along a suction flow direction, the aspirator being configured to suction liquid and solid materials through the suction opening and to convey the liquid and solid materials into a storage tank, the suction opening being so dimensioned as to be smaller than the unit of the air conditioning system and configured to engage the unit of the air conditioning system along a suction opening section;

a source of sanitizing fluid; and at least one nozzle connected to the source of sanitizing fluid, for controllable delivery of the sanitizing fluid, the at least one nozzle being positioned inside the suction opening, wherein the at least one nozzle comprises two nozzles positioned to deliver two steam jets tilted with respect to a longitudinal axis of the delivering head and incident at an intersection point, the longitudinal axis being perpendicular to a plane formed by the suction opening section.

2. The sanitation device of claim 1, wherein the at least one nozzle further comprises an additional nozzle for delivering a biocidal fluid jet along a biocidal fluid jet direction.

3. The sanitation device of claim 2, wherein the source of sanitizing fluid comprises a steam generator to produce the two steam jets and a pump to produce the biocidal fluid jet.

4. The sanitation device of claim 2, wherein the suction opening and the additional nozzle are configured so that the biocidal fluid direction is predetermined with respect to the suction flow direction.

5. The sanitation device of claim 4, wherein the suction opening and the additional nozzle are configured so that the biocidal fluid direction is parallel to the suction flow direction.

6. The sanitation device of claim 1, wherein the delivering head comprises combs or brushes for removal of solid or liquid particles.

7. The sanitation device of claim 1, further comprising a stem connected to the aspirator and the source of sanitizing fluid on one side, and connected to the delivering head on the other side.

8. The sanitation device of claim 7, wherein the stem is aligned with the delivering head along the longitudinal axis of the delivering head.

9. The sanitation device of claim 1, wherein the suction opening comprises a central suction opening inside which the two nozzles are positioned and two auxiliary suction openings configured to direct auxiliary suction flows symmetrically tilted with respect to the longitudinal axis of the delivering head.

10. The sanitation device of claim 9, further comprising a stem connected to the aspirator and the source of sanitizing fluid on one side, and connected to the delivering head on the other side, the stem being aligned with the delivering head along the longitudinal axis of the delivering head.

11. The sanitation device of claim 1, further comprising means for adjusting a flow rate of the suction flow.

12. The sanitation device of claim 1, wherein each of the two nozzles is embedded in a tube contacting an internal surface of the suction opening.

13. The sanitation device of claim 1, wherein each of the two nozzles is embedded in a tube contacting an internal surface of the suction opening, on opposite sides of the internal surface.

14. The sanitation device of claim 1, wherein the suction opening is larger than the at least one nozzle.

* * * * *